United States Patent [19]

Mauz et al.

[11] Patent Number: 4,931,476

[45] Date of Patent: Jun. 5, 1990

[54] CROSSLINKED POLYMERS AND A PROCESS FOR THEIR PREPARATION

[75] Inventors: Otto Mauz, Liederbach; Siegfried Noetzel, Kelkheim; Klaus Sauber, Schwalbach am Taunus, all of Fed. Rep. of Germany

[73] Assignee: Hoechst Aktiengesellschaft, Frankfurt am Main, Fed. Rep. of Germany

[21] Appl. No.: 89,443

[22] Filed: Aug. 26, 1987

[30] Foreign Application Priority Data

Aug. 28, 1986 [DE] Fed. Rep. of Germany ....... 3629177

[51] Int. Cl.$^5$ ............................................. C08G 59/00
[52] U.S. Cl. ..................................... 521/34; 525/379; 526/273
[58] Field of Search .......................... 526/273; 521/34; 525/379

[56] References Cited

U.S. PATENT DOCUMENTS 3,012,010 12/1961 Martin, Jr. .......................... 260/77.5
4,772,635 9/1988 Mitschker et al. ................... 526/273

FOREIGN PATENT DOCUMENTS 0146329 6/1985 European Pat. Off. .

*Primary Examiner*—Joseph L. Schofer
*Assistant Examiner*—Alex H. Walker
*Attorney, Agent, or Firm*—Finnegan, Henderson, Farabow, Garrett, and Dunner

[57] ABSTRACT

Crosslinked polymers which are produced from monomers containing epoxide groups, crosslinking monomers and, where appropriate, other monoethylenically unsaturated monomers are composed of principally spherical porous particles and are very suitable as carrier materials for the immobilization of biologically active substances.

4 Claims, No Drawings

CROSSLINKED POLYMERS AND A PROCESS FOR THEIR PREPARATION

The invention relates to crosslinked polymers which are predominantly in the form of spherical porous particles and whose structure is based on monomers containing epoxide groups, crosslinking monomers and, where appropriate, other monoethylenically unsaturated monomers. Polymers of this type are very suitable as carrier materials for the immobilization of biologically active substances.

The immobilization, via covalent bonds, of biologically active substances, such as, for example, enzymes, antibodies, antigens and hormones, with retention of their activity, on polymeric carrier materials, in order by this means, for example, to stabilize or purify enzymes or make them insoluble in water, is known. Biologically active substances immobilized in this manner offer considerable advantages compared with the soluble form: on the one hand, the removability, by sedimentation, after completion of a reaction is simplified and, on the other hand, the stability and reusability of the products are multiplied.

The introduction into a hydrophilic polymer of oxirane groups which can then be used for bonding a biologically active substance is also known (see DE-A No. 2 102 514). The hydrophilic polymers mentioned include those containing acrylamide groups. However, these carriers lack the morphology of the bead form and the porous structure. Thus, for example, they are not suitable for use in column processes.

Swellable, crosslinked bead polymers, which are obtained by copolymerization of monomers containing reactive groups, crosslinking monomers and hydrophilic monomers, have also been described as carrier substances (see DE-B No. 2 237 316). The reactive group disclosed in this are the halogenoalkyl, the epoxide, the carbonyl chloride, carboxylic anhydride, carbonyl azide, carboxylic phenyl ester and hydroxamic acid groups. However, these carrier materials have a number of disadvantages; thus, the immobilization of biologically active substances on some of them is a rather lengthy process; the activity of some of them is unsatisfactory and moreover, when using the anhydride variants, there is the formation of carboxyl groups, which are undesired.

Furthermore, bead polymers composed of crosslinked homoor copolymers of (meth)acrylamide and/or of methylenebis(meth)acrylamide and, where appropriate, further comonomers which can undergo radical polymerization (see DE-B No. 2 722 751) are known. These polymers are also suitable, because of the glycidyl methacrylate or allyl glycidyl ether, for example, which has been polymerized in, as carriers for biological active compounds. However, they have the disadvantage that organic solvents have to be used as suspending agents in their preparation, and it is impossible to work in water.

It is also known that hydrophilic latex particles containing glycidyl esters and glycidyl ethers are likewise suitable for the covalent bonding of biologically and/or immunologically active substances (see EP-A No. 0 054 685). However, for many purposes these latex particles are less suitable than the polymers in the form of beads, which can be readily used in columns, for example.

Likewise known are polymers which also contain glycidyl acrylate, glycidyl methacrylate and allyl glycidyl ether and are crosslinked with trivinyl monomers (see EP-A No. 0 146 329). However, their ability to bind enzymes is only weak.

EP-A No. 0 058 767 discloses a process for the preparation of polymers which are in the form of beads and contain oxirane groups, in which the monomers are polymerized in a special solvent mixture. However, once again it is necessary to use the disadvantagous inverse bead polymerization.

Thus, the object was to find polymers for the immobilization of biologically active substances such as, for example, enzymes, which can be prepared in a very straight-forward manner and have a very good ability to bind biologically active compounds. This has been achieved by use of crosslinked polymers produced from monomers containing epoxide groups, crosslinking monomers and, where appropriate, other monoethylenically unsaturated monomers.

Thus the invention relates to a crosslinked polymer which is substantially composed of (A) 1 to 70% by weight of units derived from glycidyl acrylate, glycidyl methacrylate, allyl glycidyl ether and/or vinyl glycidyl ether, (B) 99 to 30% by weight of units derived from N,N'-divinylethyleneurea and/or N,N'-divinylpropyleneurea, with the total of the units always being 100% by weight and with the polymer particles having an essentially spherical shape, a particle size of 10 to 600 $\mu$m and a mean pore diameter of 5 to 1,000 nm.

The invention also relates to a process for the preparation of the said polymer by copolymerization of the monomers in a liquid dispersant which, under the polymerization conditions, does not dissolve the monomers and the polymer, in the presence of a free radical initiator and other auxiliaries, and of a substance which is readily soluble in or miscible with the monomers and is virtually insoluble in the dispersant (inert agent), which comprises copolymerization of (A') 1 to 70% by weight, based on the monomer mixture, of glycidyl acrylate, glycidyl methacrylate, allyl glycidyl ether and/or vinyl glycidyl ether and (B') 99 to 30 % by weight, based on the monomer mixture, of N,N'-divinylethyleneurea and/or N,N'-divinylpropyleneurea in the presence of 50 to 300% by weight, based on the total of the monomers, of inert agent.

Finally, the invention also relates to the use of the polymers thus obtained as carrier materials for the preparation of carrier-bound biologically active substances.

The polymer according to the invention is composed of (A) 1 to 70% by weight, preferably 5 to 50% by weight, in particular 10 to 40% by weight, of units derived from a monomer (A') containing epoxide groups, (B) 30 to 99% by weight, preferably 40 to 95 % by weight, in particular 45 to 90 % by weight, of units derived from a crosslinking monomer (B'), and additionally, where appropriate, (C) 0.1 to 20 % by weight, preferably 0.1 to 10 % by weight, of units derived from a monoethylenically unsaturated, non-hydrophilic and non-crosslinking monomer (C). Each of the percentages by weight are based on the total polymer.

Examples of suitable monomers (A') containing epoxide groups are glycidyl acrylate, preferably glycidyl methacrylate and allyl glycidyl ether, in particular vinyl glycidyl ether, alone or in a mixture.

Examples of suitable crosslinking monomers (B') are N,N'-divinylpropyleneurea, but preferably N,N'-divinylethyleneurea, alone or in a mixture.

Examples of suitable monoethylenically unsaturated, non-hydrophilic and non-crosslinking monomers (C)

are vinyl alkanoates, alkyl acrylates, alkyl methacrylates, styrene and styrene derivatives, preferably vinyl acetate, methyl methacrylate, butyl acrylate and styrene, alone or in a mixture.

In the process according to the invention for the preparation of the polymer according to the invention, the monomers are polymerized in the presence of a free radical initiator and further auxiliaries in a suspension, solution or precipitation polymerization process. Suspension polymerization in water as suspending agent and at a temperature of 20° to 120020 C., preferably of 25° to 90° C., is preferred.

Suitable free radical initiators are those which are readily soluble in the monomer phase and sparingly soluble in water. Examples of these are organic peroxides such as di-tert.-butyl peroxide, dibenzoyl peroxide, bis(o-methylbenzoyl) peroxide, tert.-butyl hydroperoxide, cumene hydroperoxide, diisopropyl peroxydicarbonate and cyclohexanone peroxide, or aliphatic azo compounds such as $\alpha,\alpha'$-azodiisobutyronitrile, azobiscyanovaleric acid, 1,1'-azocyclohexane-1,1'-dicarbonitrile and azodicarbonamide.

Stabilizers and/or dispersing auxiliaries are used in the suspension polymerization, such as, for example, polyvinylpyrrolidone, polyacrylamide, polyvinyl alcohol or hydroxyethylcellulose.

In order to achieve as high a porosity of the bead polymer as is possible, certain inert, liquid components (inert agents) are added to the polymerization system or, preferably, to the monomers. These components are to be understood to be those materials in which the monomers are readily soluble or with which the monomers are miscible, but which, on the other hand, are virtually insoluble in the dispersant and thus are not miscible with it. According to their behavior toward the appropriate copolymers, the inert agents can be divided into swelling and/or precipitating agents. The inert agents do not take part in the polymerization, but are coated by the polymer and are dissolved out again during work-up. This produces permanent pores. The pore size can be affected by the type and amount of the inert agent, but also depends of the amount of crosslinking component.

The inert agents which are used in the polymerization and in which the monomers are dissolved must not in the present case react with the ethylenic double bonds and the epoxide groups of the monomers.

Preferred inert agents are pentanol, heptyl alcohol, 2-ethylhexanol, nonyl alcohol, decyl alcohol, lauryl alcohol, cyclohexanol and oxoalcohols, for example TCD alcohol M.

The inert agents are used in an amount of 50 to 300% by weight, preferably 100 to 250% by weight, in particular 125 to 200% by weight, based on the total amount of the monomers used. They can be used alone or in a mixture.

The process according to the invention is expediently carried out in a reaction vessel which is provided with a stirring device. The particle size of the bead polymer is adjusted in a known manner by the speed of stirring and the phase ratio. It is particularly advantageous to use a vertical cylindrical vessel which has a flat base and is provided with a stirrer which is located coaxially and whose shaft almost reaches the base of the vessel. The reaction vessel is preferably vacuum-tight and can be provided with a reflux condenser, addition funnel, gas-introduction tube and temperature-measuring device.

The heating and cooling of the vessel are generally brought about by a liquid bath, for example an oil bath or water bath.

It is advantageous to carry out the process according to the invention with the exclusion of atmospheric oxygen. Thus, before starting, the reaction vessel is flushed with an inert gas, preferably nitrogen.

After completion of the polymerization reaction, the unreacted monomers are removed from the reaction vessel, for example by evaporation under reduced pressure, preferably under a pressure of 0.1 to 15 torr. After removing the residual monomers, the dispersant is separated from the solid polymer, for example by decantation, filtration or aspiration of the supernatant. The polymer is then, where necessary, washed with a low-boiling organic solvent, for example a hydrocarbon, a lower alcohol or acetone, and finally dried. The polymer is usually dried at a temperature of 20° to 100° C., preferably of 40° to 80° C.; drying under reduced pressure is advisable in this process.

The bead polymer according to the invention is composed principally of spherical particles whose mean particle size in the dry, unswollen state is 10 to 600 μm, preferably 2 to 400 μm, and which preferably have a narrow particle size distribution. The particular optimum particle size of the polymer depends, in particular, on the specific area of use. For example, in a column process carried out under atmospheric pressure, it will be possible to select the particle size, within the limits mentioned above, to be correspondingly larger than for a process under elevated pressure. The beads of the bead polymer according to the invention are principally formed as macroporous beads. This is evident by the mean pore diameter which results according to the invention being in the range from 5 to 1,000 nm, preferably 10 to 800 nm.

The determination of the pore diameter (pore volume) is carried out in such a manner that first the pore volume is determined by the capillary pressure method (mercury porosimetry). In addition, a determination of the pore size is also possible by scanning electron microscopy.

The polymers according to the invention are suitable for the immobilization of biologically active substances by the formation of a covalent bond. However, they are also suitable, where appropriate after inactivation of the epoxide groups, for other purposes such as, for example, affinity chromatography etc.

The term "biologically active substances" is to be understood to be the known natural or synthetically prepared substances which are active in vivo or in vitro, for example enzymes, activators, inhibitors, antigens, antibodies, vitamins, hormones, effectors, antibiotics and proteins. In this context, the term proteins also includes proteins having certain non-protein substituents, such as metal ions, polysaccharides, porphyrin groups, adenine dinucleotide, ribonucleic acid, phospholipids etc. Polypeptide fragments, for example the active moieties of enzyme molecules, are also comprised by the term "biologically active substances".

Of the biologically active substances mentioned above, the enzymes are preferred. Examples of enzymes are urease, penicillin acylase, D-amino-acid oxidase, adenyl deaminase, alcohol dehydrogenase, asparaginase, carboxypeptidase, chymotrypsin, diphosphoesterase, α-glucosidase, glucose isomerase, glucose oxidase, glucose-6-phosphate dehydrogenase, hexokinase, invertase, β-lactamase, lactase, lactic dehydrogenase, various lectins, NAD kinase, neuraminidase, papain, peroxidase, phosphatases (alkaline and acid), 5'-phosphodiesterase, pyruvate kinase, ribonuclease and trypsin.

Examples of other biologically active substances are hormones, such as insulin and the wide variety of pituitary hormones, proteins of the gamma-globulin fraction, for example antihemophilic factor, the blood clotting factors, specific antibodies, for example hepatitis, poliomyelitis, measles, mumps, influenza or rabbit antibodies, antigens, such as hepatitis, poliomyelitis, measles, mumps, influenza or rabbit antigens for purification or stimulation of suitable antibody reactions, the antigen (after being made insoluble) remaining in the insoluble form and consequently being unable to penetrate into the body and harm it, as well as general body proteins, such as hemoglobin or albumin.

The binding of the biologically active substances to the polymeric carrier material is known per se and is generally carried out in such a way that the dry carrier material is added, for example, to an enzyme solution which is adjusted, using a buffer solution, for example 1.5 molar potassium phosphate solution in water, to a particular pH. After an immobilization time, which can be 1 to 72 hours, the carrier material is washed thoroughly at a particular temperature (for example 23° C.) with 1 molar sodium chloride solution and with the buffer solution. The specific activity on the moist carrier material is then determined, for example by automatic titration, after addition of the substrate which is to be cleaved.

The new polymers according to the invention have the following advantages: they can be prepared from low-cost commercially available starting materials; it is possible to use water as the suspending agent in the suspension polymerization, hydrocarbons and chlorinated hydrocarbons, which are necessary in inverse suspension polymerization are avoided.

The polymers in the form of beads have a very good ability to bind biologically active substances.

EXAMPLES (1)–(11) 200 ml of demineralized water, 3.2 g of disodium hydrogen phosphate and 2.0 g of polyvinylpyrrolidone of molecular weight 360,000 were initially introduced into a round-bottomed flask with a stirrer, thermometer, nitrogen introduction tube and reflux condenser, and the mixture was then stirred at 25° C. for about 20 minutes until the polyvinylprryolidone had completely dissolved. Then, in each case, a solution composed of components (A'), (B') and, where appropriate, (C') together with inert agent and 2 g of azoisobutyronitrile was added (see Table 1). The mixture was then slowly heated to a temperature of 70° C., while stirring and blanketing with nitrogen, and was maintained at this temperature for 8 hours. After the mixture had been cooled to about 25° C., the bead polymer was filtered off with suction, stirred three times with 1 liter of water for 30 minutes each time and filtered off with suction, stirred four times with 1 liter of methanol for 30 minutes each time and filtered off with suction, and stirred twice with 1 liter of acetone for 30 minutes each time and filtered off with suction. The resulting bead polymer was screened while moist with acetone and dried in a drying oven at 50° C. and under 0.26 bar of nitrogen overnight. The yields, particle size distribution found by screening analysis and, where appropriate, the mean pore diameters and the pore volumes necessary for their determination are listed in Table 1.

(12) to (18) The solution of a biologically active substance which was 1.5 molar in potassium phosphate (buffer) and had a pH of 7.6 was added to 0.2 g of a carrier material prepared as in one of the examples (buffer solutions in Example 17 1 molar in potassium phosphate and $1.6 \times 10^{-2}$ molar in benzamidine, pH 7.8; in Example 18 1 molar in potassium phosphate, pH 8). After immobilization at 23° C. for 72 hours (Example 18: immobilization time 16 hours) the beads were thoroughly washed with 1 molar sodium chloride solution and with buffer solution. The yield of material moist from the suction filter, measured using an automatic titrator at 37° C. and a pH of 7.8 with potassium penicillate as substrate (Example 17: substrate N'-benzoyl-L-arginine ethyl ester hydrochloride (BAEE), pH 8.1; Example 18: substrate urea, pH 6.1, temperature 30° C.), the corresponding dry weight, and the immobilization yield determined after balancing the initial activity and the activity in the wash water (=ratio between activity on the carrier and the activity made available) and the $\eta$ value ($\eta$=activity found/activity made available less activity in the wash water) are listed in Table 2. The activity (U) is the conversion of 1 μmol of substance per minute, and the specific activity $$= \frac{\text{conversion of 1 μmol of substance}}{\text{minute} \times \text{gram}}$$

TABLE 1

|  | Examples | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| Comp. A' . [g] | | | | | | | | | | | |
| Glycidyl methacrylate | 50 | 50 | 50 | 50 | 10 | 40 | 40 | 45 | — | — | 30 |
| Allyl glycidyl ether | — | — | — | — | — | — | — | 5 | 5 | — | — |
| Vinyl glycidyl ether | — | — | — | — | — | — | — | — | — | 50 | — |
| Comp. B': [g] | | | | | | | | | | | |
| N,N'-Divinylethyleneurea | 50 | 50 | 50 | 50 | 90 | 50 | 50 | 50 | 95 | 50 | 50 |
| Comp. C': [g] | | | | | | | | | | | |
| Vinyl acetate | — | — | — | — | — | 10 | — | — | — | — | — |
| Methyl methacrylate | — | — | — | — | — | — | 10 | — | — | — | — |
| Styrene | — | — | — | — | — | — | — | — | — | — | 20 |
| Inert agent: [g] | | | | | | | | | | | |
| Cyclohexanol | 108 | 108 | — | — | 162 | 108 | 108 | 108 | 162 | 108 | 108 |
| Lauryl alcohol | 12 | — | — | — | 18 | 12 | 12 | 12 | 18 | 12 | 12 |
| 2-Ethylhexyl alcohol | — | 12 | — | — | — | — | — | — | — | — | — |

TABLE 1-continued

| | Examples | | | | | | | | | | |
|---|---|---|---|---|---|---|---|---|---|---|---|
| | 1 | 2 | 3 | 4 | 5 | 6 | 7 | 8 | 9 | 10 | 11 |
| n-Pentanol | — | — | 120 | — | — | — | — | — | — | — | — |
| TCD alcohol M | — | — | — | 120 | — | — | — | — | — | — | — |
| Yield (g = % of th.) | 92.5 | 96.1 | 93.5 | 90.6 | 97.1 | 82.2 | 96.3 | 88.8 | 89.7 | 86.4 | 70.6 |
| Particle size: | | | | | | | | | | | |
| >300 $\mu$m [%] | — | — | — | 10 | — | — | — | — | — | — | — |
| 200–300 $\mu$m | — | 10.9 | 3.1 | 44.3 | 3.7 | 1.2 | 4.4 | — | — | 9.9 | — |
| 100–200 $\mu$m | 89.7 | 81.4 | 65.6 | 41.3 | 74.5 | 77.0 | 81.5 | 80.2 | 83.2 | 69.2 | 77.8 |
| 50–100 $\mu$m | 9.2 | 6.6 | 29.1 | 4.0 | 19.1 | 21.5 | 12.8 | 19.1 | 16.3 | 19.4 | 22.2 |
| <50 $\mu$m | 1.1 | 1.1 | 2.6 | 0.4 | 2.8 | 0.2 | 1.3 | 0.7 | 0.5 | 1.5 | — |
| Spec. pore volume [cm$^2$/g] | 1.52 | — | — | 1.11 | — | — | — | 1.08 | — | — | — |
| Pore diameter [nm] | 60 | — | — | 35 | — | — | — | 41 | — | — | — |

TABLE 2

| | Examples | | | | | | |
|---|---|---|---|---|---|---|---|
| | 12 | 13 | 14 | 15 | 16 | 17 | 18 |
| Carrier material of example | 1 | 3 | 6 | 7 | 8 | 3 | 6 |
| Biol. active substance (solution) [$\mu$l] | | | | | | | |
| Penicillin acylase | 1200 | 1200 | 1200 | 1200 | 1200 | — | — |
| Trypsin | — | — | — | — | — | 1200 | — |
| Urease | — | — | — | — | — | — | 1200 |
| Containing [mg/ml] | 30 | 30 | 30 | 30 | 30 | 6.25 | 30 |
| corr. to [U/ml] | 236 | 228 | 220 | 235 | 230 | 392 | 52 |
| Yield z [mg] (moist from filter) | 576 | 694 | 643 | 488 | 522 | 549 | 549 |
| Corr. to [U/g] | 374 | 253 | 292 | 232 | 332 | 340 | 81 |
| Based on dry weight [U/g] | 1075 | 880 | 940 | 565 | 865 | 935 | 223 |
| Immobilization [%] yield | 76 | 64 | 71 | 40 | 63 | 40 | 66 |
| $\eta$-Value | 0.89 | 0.70 | 0.74 | 0.74 | 0.66 | 0.52 | 0.75 |

(19) 0.5 ml of carboxypeptidase B with 310 units/ml in 1M potassium phosphate buffer, pH 9.0, was added to 0.1 g of a carrier material prepared as in Example 8, and the mixture was stored in a closed vessel at 16° C. for 3 days. The beads were then washed with 1M sodium chloride solution, and were stored in 50 mM potassium phosphate buffer, pH 7.0, with 0.02% sodium azide at 4° C. The binding yield was 48%, and the efficiency $\eta=0.48$. The activity units per gram dry mass, measured using hippuryl-L-arginine as substrate.

Comparison example (repeat of EP-A No. 0 146 329, Example 2)

An aqueous phase composed of 490 ml of deionized water, 16.2 g of sodium chloride, 10.5 g of a 12.5 % strength solution of sodium polyacrylate and 0.9 g of pharmaceutical gelatin, dissolved in 50 ml of deionized water, was stirred in a reaction vessel for 10 min. An organic phase composed of 111.4 g of trimethylolpropyl trimethacrylate, 28 g of glycidyl methacrylate, 314 g of toluene and 1.35 g of azoisobutyronitrile was added to the reaction vessel, and the mixture was stirred at 200 rpm for 15 minutes. The temperature was then increased to 65° C. and was maintained at this level for 20 hours. The mixture was then allowed to cool. The resulting white beads were washed three times with 1,000 ml of deionized water each time and once with 500 ml of toluene; the beads were then dried in vacuo. The yield of bead polymer was 93.5 % of theory. Screening analysis revealed the following particle size distribution:

>300 $\mu$m: 5.8 %; 200–300 $\mu$m: 40.9 %; 100–200 $\mu$m: 43.5 %; 50–100 $\mu$m: 7.8 %; <50 $\mu$m: 2.0 %.

The bead polymer was reacted with penicillin acylase as biologically active substance, and the biological activity was determined. This entailed 1,200 $\mu$l of a penicillin acylase solution (30 mg/ml, 230 U/ml) which was 1.5 molar in potassium phosphate (buffer) and had a pH of 7.6 being added to 0.2 g of the bead polymer. After immobilization at 23° C. for 72 hours, the beads were thoroughly washed with 1 molar sodium chloride solution and with buffer solution. The yield of material moist from the suction filter was 501 mg with 148 units/g measured by an automatic titrator at 37° C. and a pH of 7.8 using potassium penicillate as substrate. This was 370 units/g based on dry weight. After balancing of the initial activity and the activity in the wash water, the remaining immobilization yield was 27%.

We claim:

1. A crosslinked polymer which is substantially composed of (A) 1 to 70% by weight of units derived from at least one component selected from the group consisting of glycidyl acrylate, glycidyl methacrylate, allyl glycidyl ether and vinyl glycidyl ether, and (B) 99 to 30% by weight of units derived from at least one of N,N'-divinylethylene urea and N,N'-divinylpropyleneurea, with the total the units being 100% by weight, said polymer composed of particles having an essentially spherical shape, a mean particle size of 10 to 600 $\mu$m and a mean pore diameter of 5 to 1,000 nm.

2. A polymer as claimed in claim 1, wherein said component (A) is glycidyl methacrylate.

3. A polymer as claimed in claim 1, which additionally contains (C) 0.1 to 20% by weight, based on the total polymer, of units which are derived from at least one component selected of the group consisting of vinyl acetate, methyl methacrylate, butyl acrylate and styrene.

4. A polymer as claimed in claim 1, wherein the weight percent of (B) ranges from 40 to 95%.

* * * * *